US005939061A

United States Patent [19]

Vail et al.

[11] Patent Number: 5,939,061

[45] Date of Patent: Aug. 17, 1999

[54] ANT BAIT ATTRACTIVE TO MULTIPLE SPECIES OF ANTS

[75] Inventors: Karen M. Vail; David F. Williams; David H. Oi, all of Gainsville, Fla.

[73] Assignee: The United States of America, as represented by the Secretary of Agriculture, Washington, D.C.

[21] Appl. No.: 08/350,571

[22] Filed: Dec. 7, 1994

[51] Int. Cl.[6] .......................... A01N 43/04; A01N 43/08; A01N 59/00; A01N 65/00

[52] U.S. Cl. ......................... 424/84; 424/195.1; 424/722; 426/1; 514/23; 514/53

[58] Field of Search .................................... 424/84, 195.1, 424/722; 426/1; 514/23, 53

[56] References Cited

U.S. PATENT DOCUMENTS

| | | | |
|---|---|---|---|
| 4,075,320 | 2/1978 | Ritter et al. | 424/84 |
| 4,343,819 | 8/1982 | Wood et al. | 426/96 |
| 4,460,606 | 7/1987 | Bettarini et al. | 424/341 |
| 4,626,528 | 12/1986 | McHenry | 514/119 |
| 4,921,696 | 5/1990 | VanderMeer et al. | 424/84 |
| 4,985,413 | 1/1991 | Kohama et al. | 514/79 |
| 5,104,658 | 4/1992 | Hagarty | 424/405 |
| 5,135,744 | 8/1992 | Alexander et al. | 424/78.17 |
| 5,152,992 | 10/1992 | Kandathil et al. | 424/405 |
| 5,177,107 | 1/1993 | Meer et al. | 514/553 |
| 5,300,293 | 4/1994 | Minagawa et al. | 424/405 |
| 5,364,618 | 1/1991 | Meer et al. | 424/84 |

*Primary Examiner*—John Pak
*Attorney, Agent, or Firm*—M. Howard Silverstein; John D. Fado; Gail E. Poulos

[57] ABSTRACT

An attractant composition has been discovered for the control of multiple species of pest arthropods, particularly multiple species of pest ants. The composition, which includes a sugar and a salt or base, and water, attracts both oil-loving and sweet-loving ants and is especially useful with water soluble or suspendable toxicants.

7 Claims, No Drawings

ANT BAIT ATTRACTIVE TO MULTIPLE SPECIES OF ANTS

BACKGROUND OF THE INVENTION

1. Field of the Invention

The present invention relates to a water soluble attractant bait composition for the control of multiple species of social insects, particularly pest ant species. It also relates to the use of this composition to control multiple species of social insects in a comprehensive pest control program.

2. Description of the Prior Art

The lack of new social pest insect baits and formulations that attract multiple urban pest species has long been a problem. Commercial baits available today are targeted to only one type of pest species, such as oil-loving or sweet-loving insects, but not both. Social insects include ants, yellow jacket wasps, other pest wasps, and termites. Various species of pest ants are Solenopsis spp. (fire ants); Argentine ants, *Linepithema humile*; Pharaoh ants, *Monomorium pharaonis*; little black ants, Monomorium spp.; carpenter ants, Camponotus spp.; ghost ants, Tapinoma spp.; crazy ant, *Paratrechina longicornis*; little fire ant, *Wasmannia auropunctata*; big-headed ants, Pheidole spp.; acrobat ants, Crematogaster spp.; and other oil-loving and sweet-loving pest ants. Various ant species pose significant problems for man from both an agricultural and health care point of view. In agriculture, pest ants attack cultivations and foodstuffs and can render fields and pastures unusable. Pest ants attack wooden buildings and structures in urban and rural areas. Furthermore, ants sting livestock and humans, sometimes causing death. For example, Argentine ants endanger crops by domesticating and protecting other pest insects such as aphids and scale. Fire ants, Solenopsis spp., are particularly destructive. For example, the ants sting humans and livestock, feed on germinating seeds and crop seedlings thereby reducing yields, and damage farm machinery which strike ants' mounds. Pharaoh ants, which are worldwide household pests, thrive in wall spaces and detritus. In hospitals, they forage in soiled bandages and contaminate clean dressings and food with pathogenic microorganisms. Other Monomorium species are pests because of their mere presence in structures. Camnonotus species or carpenter ants, form their nests in wood and other moist areas and although they do not consume the wood as termites do, they can cause structural damage. Ghost ants, *Tapinoma melanoceghalum*, nest in potted plants, soil, gravel, aluminum doors, and in organic material that collects at the base of palm fronds. Because the ants can be shipped with potted plants, they are also considered nuisance pests. Crazy ants, *Paratrechina lonicornis*, named so because of their rapid and erratic movements, are nuisances as they collect crumbs and debris around gas stations, cafes, and convenience stores. While not related to the imported fire ant, the little fire ant, *Wasmannia auropunctata*, can produce an irritating sting. They are found outdoors under bark, in rotting soil, and in pine cones and have been found in clothing, food and beds indoors. *Pheidole megacephala*, the big-headed ant, is a pest in agricultural crops (pineapple) where it tends honeydew producing insects and protects them from natural enemies. The big-headed ants are also a pest in the urban environment where large infestations often leave obvious piles of dead workers throughout the structure. Crematogaster species, a species that typically nests outdoors in hollow plant cavities, can also invade homes using branches and wires as a guideline. They have been known to short-circuit telephone wires and damage rafters, posts, shingles, insulation and fiberboard.

Attractants, for insect control, are used to lure insects to a toxicant and/or trap and they can be used to identify the presence, distribution, and population of an insect.

Most commercially available baits for pest ant control are formulated with either a vegetable oil, such as soybean oil, or a sugar as the attractant in the bait. Unfortunately, although these baits may attract one ant species, they usually will not be attractive to other important pest ant species. For example, baits used for fire ant control contain soybean oil as the attractant and thus are also attractive to other non-pest oil-loving ants. Sugar baits are used to attract sugar-loving ants but not oil-loving ants. In addition, the presently available sugar baits are not effective at controlling ants because the ants do not feed on these baits for very long. Furthermore, ants such as the Florida carpenter ants, *Camponotus abdominalis floridanus*; crazy ant, *Paratrechina longicornis*; Argentine ant, *Linepithema humile*; and the ghost ant, *Tapinoma melanocephalum* have been very difficult to control with baits.

U.S. Pat. No. 5,104,658 to Hagarty discloses an insecticidal bait composition which is effective against ants, centipedes, earwigs, firebrats, German cockroaches, harvestmen, millipedes, sowbugs, spiders, and ticks. This composition includes the sugar maltose as an optional ingredient. However, the patent defines this as an attractant for sweet-loving ants and other sweet-loving insects. The patent further discloses other attractants for insects which prefer pulverized cereal, animal, or vegetable oils as attractants. The attractant is in proportions ranging from 0.1 parts to about 10 parts. The disclosed composition is formulated with different attractants depending on the specific population of insects that is to be controlled. It does not have an attractant that will attract insects regardless of a sweet, oil, cereal, or protein preference.

U.S. Pat. No. 4,985,413 to Kohama et al. discloses a bait composition that is effective against a wide range of harmful insects such as cockroaches, pillbug, beetles, and ants, including *Monomorium pharaonis, Monomorium niponense, Lasius fuliginosus*, and *Formica japonica*. The composition includes crystalline cellulose, essential oil such as soybean oil, rapeseed oil, sesame oil, wheat germ oil, etc.; crop product powders such as potato starch, sweet potato starch, corn starch, wheat flour, rice powder, corn powder, etc; a saccharide such as sucrose, glucose, D-fructose, lactose, black sugar, brown sugar, soft brown sugar, etc.; and an insecticide.

U.S. Pat. No. 5,300,293 to Minagawa et al. discloses a poison bait composition for noxious insects including cockroaches, ants, beetles and termites. This composition includes an insect growth controlling agent, dextrin, and optionally a food attractant that is at least one of plant oils, sugars, cereal flours, crushed biscuit, and animal powders.

While various pest insect attractant compositions are available, there remains a need in the art for highly effective attractant formulations for the control of multiple species of pest social insects. The present invention provides an attractant formulation which is different from prior art attractants.

SUMMARY OF THE INVENTION

It is therefore, an object of the present invention to provide an attractant bait composition for the control of multiple species of pest arthropods.

Another object of the present invention is to provide an attractant composition useful with water soluble toxicants or toxicants suspended in water for the control of multiple species of pest social insects.

Still another object of the present invention is to provide an attractant composition that includes sugar, a salt or a base, and water.

A further object of the present invention is to provide an attractant composition for the control of multiple species of sweet- and oil-loving pest insects that includes a sugar, a salt or a base, and water.

Another object of the present invention is to provide an attractant composition for the control of multiple species of sweet- and oil-loving pest insects that includes a sugar and a salt or a base.

Another object of the present invention is to provide a method for controlling multiple species of pest arthropods using a bait composition that contains an attractant that includes a sugar, a salt or a base, and water.

A further object of the present invention is to provide a method for controlling multiple species of pest arthropods using an attractant bait composition that includes a sugar, a salt or a base, and water.

A still further object of the invention is to provide a method for controlling multiple species of pest arthropods using a water soluble toxicant or toxicant suspended in water in an attractant composition that contains a sugar, a salt or a base, and water.

Further objects and advantages of the invention will become apparent from the following description.

DETAILED DESCRIPTION OF THE INVENTION

Social insects such as ants, wasps, and termites have well-developed foraging mechanisms. Social insect pests are treated in accordance with the invention by dispersing attractant-containing bait formulation in any suitable way in the vicinity of nests, in urban or rural areas, or anywhere pest social insects are a problem. The term "bait" is understood by those skilled in the art to be any substance that will entice an insect to ingest a toxicant or enter a trap and includes a phagostimulant, insecticide or trap, and a suitable carrier.

The insect attracting composition of the present invention includes (a) A sugar such as, for example, sucrose, fructose, glucose, maltose, confectioner's sugar, brown sugar, maple sugar, honey, Karo syrup, molasses, fruit syrup, corn syrup, maple syrup, beet syrup, and COCA-COLA® syrup.

(b) A salt or a base where a salt is defined as cations plus anions (R. S. Boikess and E. Edelson. 1981. Chemical Principles. Second edition. Harper and Row. New York.) Salts include, for example, lithium, sodium, potassium, barium, calcium, magnesium, zinc, or aluminum as cations and iodine, fluorine, chlorine, phosphates, nitrates, sulfates, and other negative polyatomic groups as anions. Monosodium glutamate is also included as a salt. A base is defined as an electron pair donor or a substance that can accept a proton, or a substance that produces hydroxide ions ($OH^{31}$) in aqueous solutions (Boikess and Edelson, 1981 supra). Bases include, for example, hydroxides, carbonates, bicarbonates, metal oxides, and alkoxides.

(c) Water.

The concentration of sugar in the attractant is approximately about 0.38–0.61 g per ml of attractant with a preferable concentration of 0.51 grams per ml of attractant. If the sugar is in the form of a syrup, the amount of syrup is approximately about 1–9 part(s) to 9–1 part(s) attractant based on volume, with a preferable amount of approximately about 5 parts to 5 parts attractant based on volume.

The concentration of the salt in the attractant is in an amount which enhances the attraction of pest insects to the sugar solution. The range of salt is approximately about 0.0020 to 0.0060 g per ml of attractant. The preferable amount is 0.0028 g per ml of attractant.

The concentration of base in an attractant is in an amount which enhances the attraction of pest insects to the sugar solution. The range of base is 0.0010 to 0.0040 g per ml of attractant. The preferable amount is 0.0019 g per ml of attractant.

The attractant composition is useful with toxicants or pesticides for control of pest insects. Toxicants suitable for use in the present invention include organophosphates, carbamates, arsenicals, pyrethroids, insect growth regulators, boric acid, silica gel and borate as disclosed in U.S. Pat. No. 5,104,658 which is herein incorporated by reference. Toxicants also include fluorocarbons, Sulfluramids, for example; such as those disclosed in U.S. Pat. Nos. 4,921,696, 5,177,107, and 5,364,618 which are herein incorporated by reference. Water soluble toxicants are most suitable for use with the invention since there are no known baits for these toxicants in the control of pest insects. One of ordinary skill in the art could readily substitute any suitable toxicant in the bait formulation. Toxicant concentration ranges from approximately about 0.001% to approximately about 2.5% toxicant in the attractant composition. Concentrations are based on weight and do not include the weight of a carrier.

It is preferred for commercial applications that the attractant be applied with a carrier component which can be a solid material. Non-limiting examples of solid carriers include diatomaceous earth, alumina, silica, clays, other suitable inorganic oxides, polymers, extruded corn, corn cob grits, corn grits, as well as powdered carbohydrates, such as corn starch, dextrans, and cellulose.

The attractant compositions of the present invention can be combined with the solid carrier material by any appropriate means. For example, the solid carrier can be soaked with the attractant composition resulting in a solution or suspension wherein the attractant is deposited onto or impregnated into said carrier material. The treated carrier material can then be applied by spraying the area or object to be treated; by broadcasting, by applying to cracks and crevices, and by applying a gel. The treated material can also be placed within a containerized bait station.

The following examples are presented to illustrate the use of attractant compositions for the control of pest social insects using ants as a test model system. These examples are intended to further illustrate the invention and are not intended to limit the scope as defined by the claims.

EXAMPLE 1

Laboratory colonies of ants are maintained in nests which are plastic trays (39 cm L×52 cm W×12.7 cm H) coated with Teflon 30B or Fluon on the inside walls to prevent ants from escaping. Rearing cells consist of petri dishes with a base of castone which sometimes has a water receptacle depending on the species reared. Rearing cells contain at least one queen, brood (eggs, larvae, and pupae) and workers. Colonies receive a standard diet of adult house crickets and honeywater two to three times a week. Hardboiled chicken egg is provided once a week. Colonies are maintained at 30±2° C. and 75±10% relative humidity, with 12 hour daylight cycle. A test tube filled with water and capped with a cotton ball provides moisture.

EXAMPLE 2

For testing of attractant compositions, food is removed from selected colonies one day prior to initiation of the tests. All debris is removed from one end of the tray and the nest placed at the other end of the tray. Aqueous solutions of the attractant compositions are placed in small caps (1.1 ml) filled with a dental wick. Wicks are wetted with each solution until saturated. Caps are randomly placed across the front of the tray in positions one through ten. Three colonies are tested per species per date.

The number of ants feeding on each attractant is recorded at five minute intervals for 30 minutes and again at one and two hours. Data analyses are performed on the number of ants feeding at the 30 minute, one hour, and two hour readings; the sum of the ants feeding over the entire 30 minutes; and the proportion of the ants feeding at each bait (number at each bait/number of ants at all baits) based on the 30 minute sum, one hour, and two hour reading. Data are subjected to general linear models (SAS Institute 1993) and means separated using Turkey's Honest Significant Difference Test. Different letters following means within a column, in the tables below, indicate a significant difference.

EXAMPLE 3

The attraction of ghost ants to various aqueous solutions was tested and analyzed as described above in Example 2. The nine test solutions were:

Solution

1=0.1% Trifluroacetic Acid (TFA) in water

2=Distilled and deionized water

3=0.4M NaOH

4=20% Acetonitrile (ACN) in 0.1% TFA

5=IN $H_2SO_4$

6=Phosphate buffered saline (PBS)

7=Nathanson's saline

8=1 honey:1 deionized water (volume:volume) (HW)

9=3 Karo:6 deionized water:1 casein (volume:volume) (KWC)

At thirty minutes, the HW and KWC solutions appeared to be far superior in attracting ghost ants than the remaining 7 solutions. However, at the one hour reading, more ants were feeding on the solution of 0.4M NaOH. See results in Table 1 below.

TABLE 1

| Date | 940224 | | Ghost Ant | | | | |
|---|---|---|---|---|---|---|---|
| Solution | mean # ants feeding at 30 min. | mean of the sum of ants feeding over 30 min. interval | mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
| 1 | 0.3ab | 2.3ab | 4.2bc | 0.0a | 0.0a | . | . |
| 2 | 0.3ab | 2.3ab | 4.2bc | 0.0a | 0.0a | . | . |
| 3 | 0.0b | 2.0ab | 3.6bc | 16.7a | 62.5a | . | . |
| 4 | 0.0b | 0.3b | 0.6c | 0.0a | 0.0a | . | . |
| 5 | 0.0b | 1.3b | 2.3bc | 0.0a | 0.0a | . | . |
| 6 | 0.3ab | 1.3b | 2.6bc | 1.0a | 6.3a | . | . |
| 7 | 0.0b | 1.7b | 3.3bc | 0.0a | 0.0a | . | . |
| 8 | 4.0ab | 30.0a | 45.1a | 2.0a | 12.5a | . | . |
| 9 | 4.3a | 16.0ab | 33.8ab | 2.3a | 14.6a | . | . |

. = not tested

EXAMPLE 4

Based on the results of Example 3 above, baits were formulated with HW or KWC and 0.4M NaOH or NaCl as well as the solutions by themselves. The attraction of Argentine ants, crazy ants, Florida carpenter ants, and ghost ants to various solutions was tested and analyzed as described above in Example 2. The nine test solutions for this example were:

Solution

1=1 honey:1 deionized water (HW) (volume:volume)

2=3 Karo:6 deionized water:1 casein (KWC) (weight:weight)

3=0.4M NaOH

4=9HW:1 0.4M NaOH (weight:weight)

5=3 KWC:1 0.4M NaOH (weight:weight)

6=3 KWC:1 0.4M NaCl (weight:weight)

7=9 HW:1 0.4M NaCl (weight:weight)

8=0.4M NaCI

9=10HW:1 NaCl (weight:weight)

The addition of sodium hydroxide to the honey water solution significantly increased the number of all species of ants feeding compared to honey water alone. The addition of sodium chloride to honey water increased the number of ghost ants and Argentine ants feeding at the three time periods. The results are shown in Tables 2–5 below.

TABLE 2

| Date 940510 & 11 | | | Ghost Ant | | | | |
|---|---|---|---|---|---|---|---|
| Solution | mean # ants feeding at 30 min. | mean of the sum of ants feeding over 30 min. interval | mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
| 1 | 11.0b | 73.2b | 13.5bc | 6.2ab | 12.0b | 2.3b | 10.1b |
| 2 | 3.5b | 23.2b | 3.2c | 1.0b | 4.5b | 1.2b | 7.0b |
| 3 | 0.5b | 5.3b | 1.2c | 0.2b | 1.3b | 0.8b | 2.8b |
| 4 | 33.0a | 199.33a | 47.5a | 21.0a | 49.2a | 10.3a | 50.5a |
| 5 | 2.8b | 27.5b | 5.3bc | 1.3b | 3.9b | 0.7b | 1.9b |
| 6 | 0.7b | 8.8b | 2.0c | 0.5b | 2.4c | 1.0b | 7.1b |
| 7 | 15.2b | 108.0ab | 22.5b | 10.5ab | 22.7b | 4.2b | 17.0b |
| 8 | 0.0b | 1.2b | 0.3c | 1.0b | 2.6b | 0.3b | 2.2b |
| 9 | 4.8b | 31.5b | 4.5bc | 0.7b | 1.3b | 0.5b | 1.3b |

TABLE 3

| Date 940510 & 11 | | Argentine Ant | | | | | |
|---|---|---|---|---|---|---|---|
| Solution | mean # ants feeding at 30 min. | mean of the sum of ants feeding over 30 min. interval | mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
| 1 | 18.2ab | 121.0abcd | 14.0bc | 13.0ab | 11.0bcd | 6.3a | 8.9cd |
| 2 | 19.8ab | 115.8bcd | 11.7bcd | 25.2ab | 14.8b | 16.2a | 14.2bc |
| 3 | 5.5b | 26.3d | 2.9e | 4.3b | 4.0cd | 2.3a | 3.2cd |
| 4 | 35.2a | 217.83a | 26.7a | 35.7a | 29.9a | 21.0a | 29.9a |
| 5 | 21.8ab | 132.2abc | 14.2bc | 20.8ab | 13.9bc | 19.5a | 18.9ab |
| 6 | 15.7ab | 68.0bcd | 6.6cde | 13.0ab | 7.1bcd | 13.8a | 9.8bcd |
| 7 | 24.2ab | 154.7ab | 17.2b | 18.8ab | 15.1b | 8.0a | 10.8bcd |
| 8 | 4.8b | 32.0cd | 3.6de | 3.2b | 2.5d | 1.5a | 1.7d |
| 9 | 3.7b | 28.2d | 3.0e | 1.8b | 1.7d | 1.5a | 2.6cd |

TABLE 4

| Date 940510 11 | | | Crazy Ant | | | | |
|---|---|---|---|---|---|---|---|
| Solution | mean # ants feeding at 30 min. | mean of the sum of ants feeding over 30 min. interval | mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
| 1 | 0.5a | 1.0ab | 2.7b | 0.2b | 6.7b | 0.2b | 8.3b |
| 2 | 0.0a | 9.2ab | 0.7b | 0.0b | 0.0b | 0.0b | 0.0b |
| 3 | 0.0a | 0.0b | 0.0b | 0.0b | 0.0b | 0.0b | 0.0b |
| 4 | 1.5a | 18.3a | 65.0a | 1.3a | 93.3a | 1.0a | 75.0a |
| 5 | 0.0a | 0.0b | 0.0b | 0.0b | 0.0b | 0.0b | 0.0b |
| 6 | 0.0a | 0.5ab | 4.5b | 0.0b | 0.0b | 0.0b | 0.0b |
| 7 | 0.8a | 4.5ab | 23.0b | 0.0b | 0.0b | 0.2b | 16.7b |
| 8 | 0.0a | 0.0b | 0.0b | 0.0b | 0.0b | 0.0b | 0.0b |
| 9 | 0.3a | 1.8ab | 4.1b | 0.0b | 0.0b | 0.0b | 0.0b |

TABLE 5

| Date 940510 11 | | | Florida Carpenter Ant | | | | |
|---|---|---|---|---|---|---|---|
| Solution | mean # ants feeding at 30 min. | mean of the sum of ants feeding over 30 min. interval | mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
| 1 | 2.0b | 13.2b | 20.7b | 3.2b | 20.9b | 2.2b | 12.9b |
| 2 | 0.0b | 1.8b | 1.8cd | 0.2b | 1.6c | 0.0b | 0.0b |
| 3 | 0.5b | 1.8b | 2.5cd | 0.5b | 2.2c | 1.0b | 12.3b |
| 4 | 7.2a | 36.3a | 56.2a | 7.5a | 65.4a | 7.3a | 57.4a |
| 5 | 0.5b | 1.8b | 1.8cd | 0.2b | 0.6c | 0.5b | 2.3b |
| 6 | 0.3b | 0.7b | 0.6d | 0.5b | 2.0c | 0.0b | 0.0b |

TABLE 5-continued

| Date 940510 11 | | | Florida Carpenter Ant | | | | |
|---|---|---|---|---|---|---|---|
| Solution | mean # ants feeding at 30 min. | mean of the sum of ants feeding over 30 min. interval | mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
| 7 | 1.2b | 8.7b | 12.5bc | 1.2b | 5.3bc | 1.8b | 9.7b |
| 8 | 0.2b | 1.2b | 1.3d | 0.3b | 1.3c | 0.7b | 3.2b |
| 9 | 0.3b | 1.8b | 2.5cd | 0.5b | 1.9c | 0.3b | 1.8b |

EXAMPLE 5

To determine if any other sugar is useful in the bait formulation, powdered sugar in deionized water (SW) was tested since it had been found to be attractive to ghost ants. The attraction of ghost, argentine, crazy and Florida carpenter ants was tested and analyzed as described above in Example 2. The ten test solutions were:

Solution

1=1 honey:1 deionized water (HW) (volume:volume)

2=9 HW:1 0.4M NaOH (weight:weight)

3=9 HW:1 0.4M NaCl (weight:weight)

4=8 HW:2 0.4M NaOH (weight:weight)

5=8 HW:2 0.4M NaCl (weight:weight)

6=9 SW:1 0.4M NaOH (weight:weight)

7=9 SW:1 0.4M NaCl (weight:weight)

8=8 SW:2 0.4M NaOH (weight:weight)

9=8 SW:2 0.4M NaCl (weight:weight)

10=9 powdered sugar:10 deionized water (SW) (weight:weight)

With the addition of 1 part 0.4M NaOH to 9 parts SW (volume:volume), there were more ants feeding than all of the other solutions for all the variables tested for argentine ants, crazy ants, and Florida carpenter ants. This solution was also the most attractive solution for the ghost ant through the one hour reading. The results are shown below in Tables 6–9.

TABLE 6

| Date 940516 17 | | | Ghost Ant | | | | |
|---|---|---|---|---|---|---|---|
| Solution | mean # ants feeding at 30 min. | mean of the sum of ants feeding over 30 min. interval | mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
| 1 | 0.5b | 12.2a | 2.8b | 0.3b | 1.8b | 0.3a | 2.2b |
| 2 | 2.2ab | 20.5a | 6.4ab | 1.3b | 5.8b | 0.3a | 2.8b |
| 3 | 1.8ab | 31.5a | 7.9ab | 0.5b | 2.6b | 0.5a | 2.8b |
| 4 | 2.5ab | 26.7a | 7.1ab | 0.3b | 0.8b | 0.5a | 5.5ab |
| 5 | 1.2b | 14.8a | 4.6b | 0.3b | 1.3b | 0.2a | 1.5b |
| 6 | 11.0a | 59.33a | 14.8ab | 5.7a | 29.9a | 1.3a | 9.7ab |
| 7 | 8.0ab | 54.5a | 18.2a | 1.8ab | 13.0ab | 2.0a | 33.3a |
| 8 | 9.2ab | 54.2a | 14.0ab | 4.2ab | 18.8ab | 2.5a | 16.0ab |
| 9 | 6.5ab | 39.7a | 9.9ab | 3.0ab | 14.5ab | 1.8a | 18.5ab |
| 10 | 7.8ab | 52.5a | 14.3ab | 2.5ab | 11.6ab | 1.2a | 7.8ab |

TABLE 7

| Date 940516-17 | | | Argentine Ant | | | | |
|---|---|---|---|---|---|---|---|
| Solution | mean # ants feeding at 30 min. | mean of the sum of ants feeding over 30 min. interval | mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
| 1 | 6.5b | 40.8ab | 4.2d | 4.8a | 2.0c | 0.3b | 0.3e |
| 2 | 12.5ab | 74.5ab | 9.8bcd | 9.3a | 7.8bc | 5.7ab | 7.7cde |
| 3 | 4.3b | 34.7b | 3.7d | 3.2a | 2.0c | 0.7b | 0.7e |
| 4 | 10.2ab | 61.8ab | 8.4bcd | 9.2a | 7.2bc | 4.2ab | 5.3de |
| 5 | 8.5ab | 49.3ab | 4.8cd | 5.3a | 2.7c | 2.0b | 2.1e |
| 6 | 25.0ab | 131.2a | 19.2a | 23.5a | 18.4a | 16.8a | 23.0a |
| 7 | 17.0ab | 108.2ab | 13.2ab | 19.0a | 13.9ab | 11.0ab | 12.8cd |
| 8 | 18.8ab | 95.3ab | 13.9ab | 20.0a | 15.9ab | 14.3ab | 21.2ab |
| 9 | 16.7ab | 83.3ab | 11.0bcd | 16.3a | 11.7ab | 11.0ab | 12.8cd |
| 10 | 16.0ab | 79.2ab | 11.8bc | 17.8a | 18.5a | 10.5ab | 13.9bc |

TABLE 8

| Date 940516 17 Solution | mean # ants feeding at 30 min. | mean of the sum of ants feeding over 30 min. interval | Crazy Ant mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
|---|---|---|---|---|---|---|---|
| 1 | 0.0b | 0.5b | 0.8b | 0.2a | 1.8a | 0.0b | 0.0b |
| 2 | 0.2ab | 3.0ab | 4.6b | 0.5a | 21.8a | 0.0b | 0.0b |
| 3 | 0.0b | 0.2b | 1.3b | 0.0a | 0.0a | 0.0b | 0.0b |
| 4 | 0.2ab | 2.0ab | 8.0b | 0.0a | 0.0a | 0.0b | 0.0b |
| 5 | 0.0b | 0.7b | 1.1b | 0.2a | 1.8a | 0.2ab | 20.0ab |
| 6 | 1.5a | 9.3a | 35.6a | 0.8a | 35.2a | 0.8a | 80.0b |
| 7 | 1.0ab | 3.8ab | 18.4ab | 0.2a | 1.8a | 0.0b | 0.0b |
| 8 | 0.7ab | 7.2ab | 22.0ab | 0.5a | 23.6a | 0.0b | 0.0b |
| 9 | 0.2ab | 1.3ab | 4.7b | 0.2a | 6.7a | 0.0b | 0.0b |
| 10 | 0.3ab | 2.2ab | 3.5b | 0.7a | 7.3a | 0.0b | 0.0b |

TABLE 9

| Date 940516 17 Solution | mean # ants feeding at 30 min. | mean of the sum of ants feeding over 30 min. interval | Florida Carpenter Ant mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
|---|---|---|---|---|---|---|---|
| 1 | 0.2b | 0.8cd | 0.7d | 0.2c | 0.5c | 0.2b | 0.9b |
| 2 | 0.7b | 7.2bcd | 6.1bcd | 1.0bc | 3.8bc | 0.2b | 0.7b |
| 3 | 0.2b | 1.5cd | 1.7d | 0.0c | 0.0c | 0.2b | 0.9b |
| 4 | 1.2ab | 6.3bcd | 5.3cd | 1.0bc | 5.5bc | 0.8ab | 5.4b |
| 5 | 0.0b | 0.0d | 0.0d | 0.0c | 0.0c | 0.0b | 0.0b |
| 6 | 4.2a | 24.3a | 30.9a | 5.7a | 31.7a | 4.0a | 36.5a |
| 7 | 2.5ab | 13.8abc | 17.8bc | 3.3abc | 11.5bc | 3.0ab | 13.3ab |
| 8 | 3.0ab | 15.3ab | 18.7ab | 4.2ab | 19.5ab | 2.7ab | 14.7ab |
| 9 | 2.2ab | 9.2bcd | 10.0bcd | 2.3abc | 18.9ab | 2.7ab | 15.3ab |
| 10 | 2.2ab | 9.7bcd | 8.8bcd | 2.3abc | 8.7bc | 2.8ab | 12.2ab |

EXAMPLE 6

In order to test the attraction of imported fire ants, Pharaoh ant, *Pheidole dentata Pheidole megacephala, Technomyrmex albipes, Wasmannia auropunctata, Crematogaster pilosa* and *Monomorium trageri*, these ant species were tested with the same solutions as described above in Example 5. All of the solutions tested were equally acceptable to these ants. This may probably be due to their omnivorous feeding habits. The results are shown below in Tables 10–17.

TABLE 10

| Date 940518 Solution | mean # ants feeding at 30 min. | mean of the sum of ants feeding over 30 min. interval | Fire Ant mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
|---|---|---|---|---|---|---|---|
| 1 | 43.3a | 230.7a | 10.2a | . | . | . | . |
| 2 | 50.0a | 254.0a | 11.4a | . | . | . | . |
| 3 | 48.3a | 256.7a | 11.4a | . | . | . | . |
| 4 | 39.7a | 195.3a | 8.5a | . | . | . | . |
| 5 | 51.7a | 277.3a | 12.7a | . | . | . | . |
| 6 | 44.3a | 106.3a | 9.4a | . | . | . | . |
| 7 | 43.3a | 196.7a | 9.0a | . | . | . | . |
| 8 | 43.3a | 187.3a | 8.4a | . | . | . | . |
| 9 | 45a | 215.3a | 9.3a | . | . | . | . |
| 10 | 43.3a | 208.7a | 9.2a | . | . | . | . |

. = not tested

TABLE 11

| Date | 940518 | | Pharaoh Ant | | | | |
|---|---|---|---|---|---|---|---|
| Solution | mean # ants feeding at 30 min. | mean of the sum of ants feeding over 30 min. interval | mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
| 1 | 34.3a | 250.3a | 6.9a | . | . | . | . |
| 2 | 56.0a | 346.3a | 12.1a | . | . | . | . |
| 3 | 46.3a | 271.0a | 8.9a | . | . | . | . |
| 4 | 34.3a | 253.0a | 8.2a | . | . | . | . |
| 5 | 35.3a | 228.7a | 7.8a | . | . | . | . |
| 6 | 64.0a | 413.7a | 14.2a | . | . | . | . |
| 7 | 43.7a | 268.7a | 9.6a | . | . | . | . |
| 8 | 42.3a | 289.3a | 10.7a | . | . | . | . |
| 9 | 50.7a | 323.3a | 11.5a | . | . | . | . |
| 10 | 48.0a | 310.7a | 10.1a | . | . | . | . |

. = not tested

TABLE 12

| Date | 940525 | | *Pheidole dentata* | | | | |
|---|---|---|---|---|---|---|---|
| Solution | mean # ants feeding at 30 min. | mean of the sum of ants feeding over 30 min. interval | mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
| 1 | 8.0a | 58.7a | 9.6ab | 4.0a | 5.6a | 3.3a | 5.2a |
| 2 | 7.0a | 42.3a | 6.6ab | 5.3a | 7.9a | 2.7a | 4.2a |
| 3 | 9.3a | 75.3a | 12.6ab | 4.0a | 6.1a | 2.3a | 4.7a |
| 4 | 5.0a | 31.0a | 4.8b | 3.0a | 4.6a | 2.7a | 4.7a |
| 5 | 6.7a | 43.7a | 7.1ab | 3.3a | 4.1a | 2.7a | 4.2a |
| 6 | 9.3a | 62.3a | 10.6ab | 6.0a | 9.9a | 7.0a | 13.1a |
| 7 | 11.0a | 72.0a | 12.4ab | 10.3a | 15.8a | 9.0a | 18.4a |
| 8 | 6.3a | 35.3a | 5.5b | 6.0a | 7.5a | 6.0a | 11.0a |
| 9 | 16.3a | 79.7a | 14.5ab | 12.0a | 16.6a | 9.0a | 17.8a |
| 10 | 17.3a | 94.7a | 16.4a | 13.0a | 21.9a | 8.7a | 16.7a |

TABLE 13

| Date | 940525 | | *Pheidole megacephala* | | | | |
|---|---|---|---|---|---|---|---|
| Solution | mean # ants feeding at 30 min. | mean of the sum of ants feeding over 30 min. interval | mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
| 1 | 14.3a | 46.0a | 16.4a | 20.3a | 15.0a | 3.0a | 5.3a |
| 2 | 8.7a | 29.3a | 7.2a | 13.0a | 8.9ab | 7.3a | 9.8a |
| 3 | 10.7a | 46.7a | 18.4a | 15.7a | 11.6a | 9.0a | 9.9a |
| 4 | 9.7a | 23.0a | 10.0a | 14.7a | 10.4ab | 5.3a | 5.8a |
| 5 | 9.7a | 25.7a | 9.5a | 17.0a | 12.2a | 5.7a | 8.2a |
| 6 | 5.3a | 23.0a | 6.0a | 11.0a | 7.5ab | 5.7a | 12.0a |
| 7 | 7.7a | 41.0a | 10.8a | 15.7a | 10.7ab | 10.3a | 17.1a |
| 8 | 6.7a | 20.3a | 7.5a | 14.0a | 10.3ab | 9.3a | 13.2a |
| 9 | 12.7a | 39.0a | 10.0a | 14.7a | 9.9ab | 11.7a | 14.7a |
| 10 | 3.3a | 12.7a | 4.2a | 5.3a | 3.5b | 2.0a | 4.1a |

TABLE 14

| Date | 940525 | | *Technomyrmex albipes* | | | | |
|---|---|---|---|---|---|---|---|
| Solution | mean # ants feeding at 30 min. | mean of the sum of ants feeding over 30 min. interval | mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
| 1 | 18.3a | 119.0a | 8.8a | 16.3a | 4.3a | 14.7a | 6.4a |
| 2 | 22.7a | 144.0a | 7.8a | 27.0a | 11.4a | 28.3a | 9.4a |
| 3 | 19.7a | 133.7a | 9.5a | 19.0a | 8.4a | 18.7a | 8.6a |
| 4 | 21.0a | 182.0a | 15.2a | 30.7a | 16.3a | 28.0a | 14.1a |

TABLE 14-continued

| Date 940525 | | | *Technomyrmex albipes* | | | | |
|---|---|---|---|---|---|---|---|
| Solution | mean # ants feeding at 30 min. | mean of the sum of ants feeding over 30 min. interval | mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
| 5 | 15.0a | 108.7a | 7.7a | 17.7a | 5.4a | 18.0a | 10.9a |
| 6 | 18.3a | 124.0a | 8.9a | 21.3a | 13.4a | 24.0a | 7.1a |
| 7 | 23.7a | 170.0a | 13.0a | 21.7a | 10.6a | 28.7a | 13.7a |
| 8 | 23.3a | 137.3a | 10.7a | 24.0a | 13.3a | 20.3a | 12.1a |
| 9 | 16.0a | 112.7a | 7.9a | 21.0a | 7.2a | 17.3a | 8.6a |
| 10 | 21.7a | 142.3a | 10.4a | 22.0a | 9.6a | 19.7a | 9.1a |

TABLE 15

| Date 940525 | | | *Wasmannia auropunctata* | | | | |
|---|---|---|---|---|---|---|---|
| Solution | mean # ants feeding at 30 min. | mean of the sum of ants feeding over 30 min. interval | mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
| 1 | 19.7a | 115.3a | 10.3a | 18.3a | 9.0a | 7.3a | 4.9a |
| 2 | 20.7a | 118.3a | 12.0a | 20.7a | 12.0a | 20.7a | 13.1a |
| 3 | 18.0a | 105.7a | 9.9a | 15.7a | 8.8a | 9.0a | 5.5a |
| 4 | 38.7a | 212.3a | 17.7a | 33.3a | 15.9a | 17.7a | 14.9a |
| 5 | 17.3a | 107.0a | 12.5a | 15.0a | 10.0a | 11.3a | 12.2a |
| 6 | 23.3a | 131.7a | 13.3a | 21.0a | 12.3a | 15.0a | 13.2a |
| 7 | 12.0a | 63.7a | 6.8a | 14.7a | 8.5a | 12.0a | 9.1a |
| 8 | 11.7a | 62.3a | 5.6a | 15.0a | 8.2a | 11.7a | 8.3a |
| 9 | 16.7a | 84.0a | 7.3a | 17.0a | 9.6a | 14.7a | 11.3a |
| 10 | 15.0a | 62.0a | 4.6a | 12.0a | 5.7a | 9.0a | 7.5a |

TABLE 16

| Date 940525 | | | *Crematogaster pilosa* | | | | |
|---|---|---|---|---|---|---|---|
| Solution | mean # ants feeding at 30 min. | mean of the sum of ants feeding over 30 min. interval | mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
| 1 | 21.0a | 75.7a | 30.5a | 24.3a | 37.1a | 14.7a | 28.1a |
| 2 | 3.3a | 29.0a | 5.4a | 6.3a | 6.9a | 5.0a | 9.1a |
| 3 | 13.3a | 62.3a | 10.2a | 9.3a | 9.4a | 7.0a | 13.1a |
| 4 | 7.7a | 48.0a | 7.4a | 4.7a | 4.5a | 2.3a | 2.8a |
| 5 | 7.0a | 49.7a | 9.9a | 10.0a | 10.6a | 4.7a | 6.8a |
| 6 | 3.3a | 22.7a | 28.6a | 2.0a | 1.9a | 3.7a | 6.8a |
| 7 | 8.0a | 42.3a | 23.5a | 11.3a | 17.6a | 13.0a | 23.5a |
| 8 | 3.3a | 21.7a | 2.7a | 3.7a | 3.6a | 1.3a | 2.2a |
| 9 | 4.7a | 23.7a | 3.1a | 5.3a | 5.2a | 4.0a | 5.5a |
| 10 | 4.3a | 23.0a | 4.5a | 3.3a | 3.3a | 1.7a | 2.0a |

TABLE 17

| Date 940525 | | | *Monomorium trageri* | | | | |
|---|---|---|---|---|---|---|---|
| Solution | mean # ants feeding at 30 min. | mean of the sum of ants feeding over 30 min. interval | mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
| 1 | 16.0a | 121.3a | 13.9a | 15.3a | 7.4a | 5.7a | 5.7a |
| 2 | 22.7a | 122.0a | 17.8a | 31.3a | 22.3a | 21.0a | 19.4a |
| 3 | 10.7a | 87.3a | 7.9a | 10.3a | 4.7a | 4.7a | 3.2a |
| 4 | 13.0a | 71.0a | 7.1a | 13.7a | 6.3a | 11.7a | 8.4a |
| 5 | 11.7a | 80.7a | 10.4a | 11.3a | 5.8a | 5.3a | 4.6a |
| 6 | 18.3a | 96.7a | 15.0a | 28.0a | 19.2a | 17.7a | 19.1a |
| 7 | 12.7a | 76.0a | 10.5a | 20.7a | 14.5a | 16.0a | 17.3a |

TABLE 17-continued

| Date | 940525 | | Monomorium trageri | | | | |
|---|---|---|---|---|---|---|---|
| Solution | mean # ants feeding at 30 min. | mean of the sum of ants feeding over 30 min. interval | mean percentage of ants feeding based on 30 minute sum | mean # ants feeding at 1 hour | mean percentage of ants feeding at 1 hour | mean # ants feeding at 2 hour | mean percentage of ants ants feeding at 2 hour |
| 8 | 9.7a | 44.0a | 5.4a | 13.0a | 7.6a | 9.0a | 8.1a |
| 9 | 11.0a | 57.0a | 6.7a | 13.7a | 8.3a | 9.0a | 8.6a |
| 10 | 6.0a | 41.0a | 5.3a | 6.3a | 4.0a | 6.0a | 5.8a |

The foregoing detailed description is for the purpose of illustration. Others skilled in the art can apply the knowledge described to other social insect pests. Such detail is solely for that purpose and those skilled in the art can make variations therein without departing from the spirit and scope of the invention.

We claim:

1. An attractant composition for multiple species of pest arthropod species consisting essentially of (a) an effective amount of a sugar for attracting multiple species of pest arthropods, (b) an effective amount of a base for enhancing the attraction of multiple species of pest arthropods to the sugar, wherein said effective amount of the base is from 0.001 to 0.004 g per 1 ml of said attractant composition, and (c) a solvent in amounts to dissolve said effective amounts of said sugar and base.

2. The composition of claim 1 wherein said solvent is water.

3. The composition of claim 1 wherein said sugar is selected from the group consisting of sucrose, fructose, glucose, maltose, confectioner's sugar, brown sugar, maple sugar, honey, karo syrup, molasses, fruit syrup, corn syrup, cola syrup, maple syrup, beet syrup, and mixtures thereof.

4. The attractant composition of claim 3 wherein said sugar is confectioner's sugar, said base is sodium hydroxide and said solvent is water.

5. A method for attracting multiple species of pest arthropods comprising preparing an attractant composition consisting essentially of an effective amount of a sugar for attracting pest arthropods, an effective amount of a base for enhancing the attractiveness of the sugar and a solvent to form a liquid attractant composition, wherein said effective amount of the base is from 0.001 to 0.004 g per 1 ml of said liquid attractant composition, applying said liquid attractant composition to a carrier, and treating an area containing pest arthropods with said carrier containing said composition.

6. The method of claim 5 wherein said sugar is selected from the group consisting of sucrose, fructose, glucose, maltose, confectioner's sugar, brown sugar, maple sugar, honey, karo syrup, molasses, fruit syrup, corn syrup, cola syrup, maple syrup, beet syrup, and mixtures thereof.

7. The method of claim 5 wherein said sugar is confectioner's sugar and said base is sodium hydroxide.

* * * * *